US00PP18169P2

(12) United States Plant Patent
Schoenmakers

(10) Patent No.: US PP18,169 P2
(45) Date of Patent: Oct. 30, 2007

(54) ***FITTONIA* PLANT NAMED 'PINK STAR'**

(50) Latin Name: *Fittonia verschaffeltii*
Varietal Denomination: Pink Star

(75) Inventor: Kees Schoenmakers, Haaren (NL)

(73) Assignee: Schoenmakers Tropische Potcultures VoF, Haaren (NL)

( * ) Notice: Subject to any disclaimer, the term of this patent is extended or adjusted under 35 U.S.C. 154(b) by 0 days.

(21) Appl. No.: 11/287,064

(22) Filed: Nov. 25, 2005

(51) Int. Cl.
*A01H 5/00* (2006.01)

(52) U.S. Cl. ..... Plt./373

(58) Field of Classification Search ..... Plt./263, Plt./373
See application file for complete search history.

(56) References Cited

PUBLICATIONS

GTITM UPOVROM Citation for 'Pink Star' as per NL PBR FTN0019; Aug. 29, 2002.*
GTITM UPOVROM Citation for 'Pink Star' as per NL PBR FTN0026; Aug. 9, 2004.*

* cited by examiner

*Primary Examiner*—Kent Bell

(57) ABSTRACT

A new cultivar of *Fittonia* plant named 'Pink Star' that is characterized by small pink leaves with wavy green margins and spots.

1 Drawing Sheet

Botanical Classification: *Fittonia verschaffeltii.*
Variety Denomination: 'Pink Star'.

BACKGROUND OF THE INVENTION

The present invention relates to a new and distinct cultivar of *Fittonia* plant botanically known as *Fittonia verschaffeltii* and hereinafter referred to by the cultivar name 'Pink Star'.

The new cultivar was discovered by the inventor in a cultivated area of Haaren, The Netherlands in February 2003. 'Pink Star' was discovered as a naturally occurring whole plant mutation of *Fittonia* 'Janita' (not patented).

Asexual reproduction by terminal cuttings of the new cultivar 'Pink Star' was first done in June 2003 in Haaren, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Fittonia* cultivar 'Pink Star'.

1. *Fittonia* 'Pink Star' exhibits small leaves.
2. *Fittonia* 'Pink Star' exhibits pink leaves with green margins and spots.
3. *Fittonia* 'Pink Star' exhibits wavy leaf margins.

The closest comparison cultivar is *Fittonia* 'Red Star' (U.S. Plant patent application Ser. No. 11/287,062). The new cultivar *Fittonia* 'Pink Star' is distinguishable from *Fittonia* 'Red Star' by the following characteristics:

1. 'Pink Star' exhibits pink leaves with green margins and spots. The leaves of 'Red Star' are pink to red with green margins and spots.

The new cultivar 'Pink Star' is distinguishable from the parent plant 'Janita' by the following characteristics:

1. 'Pink Star' is more compact than 'Janita'.
2. 'Pink Star' has leaves that are more pink than those of 'Janita'.

BRIEF DESCRIPTION OF THE DRAWING

The accompanying photograph illustrates the distinguishing traits of *Fittonia* 'Pink Star'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Fittonia* cultivar named 'Pink Star'. Data was collected in Haaren, The Netherlands from 12 week old greenhouse grown plants in 8.5 cm. containers. The time of year was Fall and the average temperature was 24 degrees Centigrade during the day and 22 degrees Centigrade at night. No photoperiodic treatments were used. Color determinations are in accordance with The Royal Horticultural Society Colour Chart 2001 edition, except where general color terms of ordinary dictionary significance are used. The growing requirements are similar to the species. 'Pink Star' has not been tested under all possible conditions and phenotypic differences may be observed with variations in environmental, climatic, and cultural conditions, however, without any variance of in genotype.

Botanical classification: *Fittonia verschaffeltii* 'Pink Star'.
Use: Ornamental.
Parentage: 'Pink Star' is a naturally occurring whole plant mutation of *Fittonia* 'Janita'.
Vigor: Moderate.

Growth rate: Moderate.
Growth habit: Broad spreading, upright.
Plant shape: Flattened globose.
Suitable container size: 8.5 cm. diameter container.
Height: Average 5.7 cm.
Width: Average 9 cm.
Hardiness: USDA Zone 10.
Propagation: Terminal cuttings.
Time to initiate roots: Approximately 21 days to produce roots on an initial cutting at 24° Centigrade.
Time to produce a rooted cutting: Approximately 35 days to produce a rooted cutting at 24° Centigrade.
Crop time: 12 weeks.
Root system: Fine and fibrous.
Stem:
*Branching habit.*—Moderating branching.
*Average number of lateral branches.*—3.
*Pinching.*—No.
*Lateral branch diameter.*—2 mm. in diameter, thickened at the nodes, 3 mm in diameter.
*Lateral branch length.*—2.8 cm. in length.
*Lateral branch color.*—200C with tinges of 143D.
*Lateral branch strength.*—Moderate.
*Stem color.*—165A to 166A.
*Pubescence.*—Dense, length 0.5 mm, color N155A.
*Internode length.*—6 mm. between nodes.
*Internode color.*—144B.
*Shape.*—Rounded.
*Surface.*—Dull.
*Stem strength.*—Moderate to strong.
Foliage:
*Leaf arrangement.*—Opposite.
*Compound or single.*—Single.
*Leaf shape.*—Obovate to lanceolate.
*Leaf apex.*—Acute.
*Leaf base.*—Obtuse to rounded.
*Leaf texture.*—Slightly glossy and slightly rugose with prominent venation.
*Leaf length.*—Average 3 cm. in length.
*Leaf width.*—1.6 cm. in width.
*Quantity of leaves per lateral branch.*—Average 8.
*Pubescence.*—Short hairs on margins, 0.2 mm. in length, N155A.
*Leaf margin.*—Considerably wavy.
*Vein pattern.*—Pinnate.
*Young leaf color,* (*upper surface*).—139A to 139B.
*Young leaf color,* (*lower surface*).—137C to 137D.
*Mature leaf color,* (*upper surface*).—139A.
*Mature leaf color,* (*lower surface*).—137B.
*Vein color* (*upper surface*).—51A.
*Vein color* (*lower surface*).—51D with a tint of 144D.
*Leaf attachment.*—Petiolate.
*Petiole dimensions.*—Average 7 mm. in length, 2 mm. in diameter, 1.5 mm. in height.
*Petiole color* (*upper surface*).—175A to 175B.
*Petiole color* (*lower surface*).—175A to 175B.
*Durability of foliage to stress.*—High.
Flowers: Flowers have not been observed.
Disease and Insect Resistance: Plants of the new *Fittonia* have not been observed for disease or insect resistance.

What is claimed is:

1. A new and distinct variety of *Fittonia* plant named 'Pink Star' as described and illustrated.

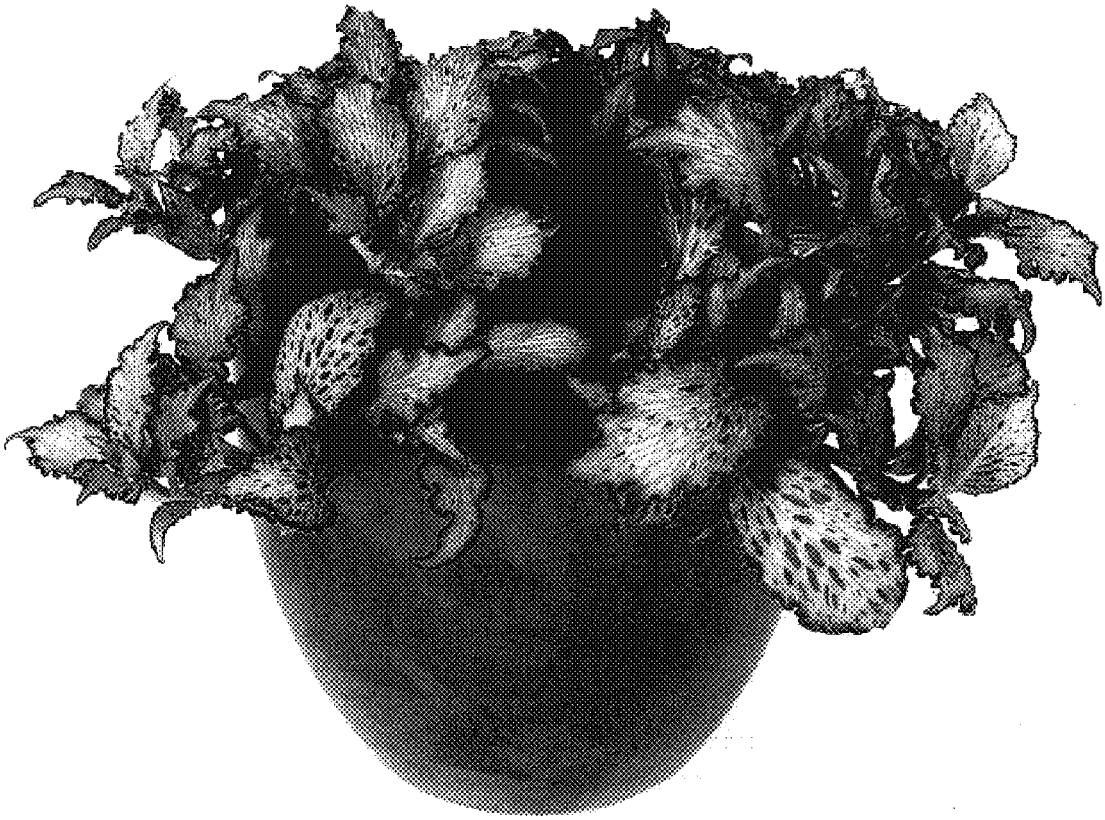

* * * * *